United States Patent

Kumai et al.

[11] Patent Number: 5,208,394
[45] Date of Patent: May 4, 1993

[54] PROCESS FOR PRODUCING CHLOROFLUOROBENZENES

[75] Inventors: Seisaku Kumai, Fujisawa; Akihiro Wada; Shinsuke Morikawa, both of Yokohama, all of Japan

[73] Assignee: Asahi Glass Company Ltd., Tokyo, Japan

[21] Appl. No.: 924,790

[22] Filed: Aug. 6, 1992

Related U.S. Application Data

[63] Continuation of Ser. No. 675,064, Mar. 26, 1991, abandoned, which is a continuation of Ser. No. 394,805, Aug. 17, 1989, abandoned.

[30] Foreign Application Priority Data

Aug. 26, 1988 [JP] Japan ................................ 63-210805

[51] Int. Cl.$^5$ ...................... C07C 17/22; C07C 17/20; C07C 25/13
[52] U.S. Cl. ..................................... 570/141; 568/938; 570/127
[58] Field of Search .......................................... 570/141

[56] References Cited

U.S. PATENT DOCUMENTS

4,730,046  3/1988  Bay et al. ............................ 570/141

FOREIGN PATENT DOCUMENTS

| | | |
|---|---|---|
| 0003344 | 8/1979 | European Pat. Off. . |
| 0019789 | 12/1980 | European Pat. Off. . |
| 150587 | 8/1985 | European Pat. Off. ............. 570/141 |
| 0159388 | 10/1985 | European Pat. Off. . |
| 159388 | 10/1985 | European Pat. Off. ............. 570/141 |
| 0163230 | 4/1986 | European Pat. Off. . |
| 0180057 | 5/1986 | European Pat. Off. . |
| 246326 | 12/1985 | Japan ................................. 570/141 |
| 61-126042 | 6/1986 | Japan . |
| 1126042 | 6/1986 | Japan ................................. 570/141 |
| 2154581 | 9/1985 | United Kingdom ................. 570/141 |

OTHER PUBLICATIONS

N. N. Vorozhtsov et al., "Aromatic Fluoro Derivatives", D. I. Mendeleev Moscow Chemical-Technological Institute Translated From Zhurnal Obshehel Khimil, vol. 31, No. 4, pp. 1222–1226, Apr. 1961.
Cason "Organic Chemistry" (1956) p. 274.
Morrison & Boyd "Organic Chemistry" 3rd ed. (1973) p. 342.

*Primary Examiner*—Joseph E. Evans
*Attorney, Agent, or Firm*—Oblon, Spivak, McClelland, Maier & Neustadt

[57] ABSTRACT

A process for producing chlorofluorobenzenes, which comprises reacting fluorine-containing nitrobenzenes of the following formula (1) with chlorine gas to obtain chlorofluorobenzenes of the following formula (2):

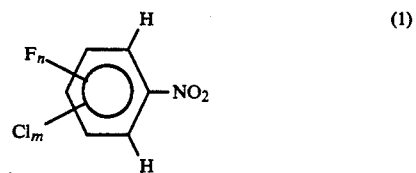

(1)

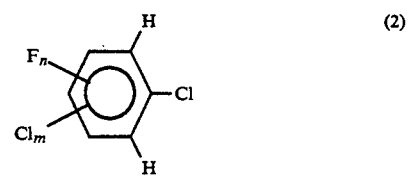

(2)

wherein n and m are integers satisfying $1 \leq n \leq 3$, $0 \leq m \leq 2$ and $1 \leq n+m \leq 3$.

2 Claims, No Drawings

PROCESS FOR PRODUCING CHLOROFLUOROBENZENES

This application is a continuation of application Ser. No. 07/675,064, filed on Mar. 26, 1991, now abandoned, which is a continuation of application Ser. No. 07/394,805, filed Aug. 17, 1989, now abandoned.

The present invention relates to a process for producing chlorofluorobenzenes.

The following methods are known for the production of chlorofluorobenzenes: (1) a method in which reduction and a Balz and Schiemann method are combined (Rec. Trav. Chim., 51, 98–113 (1932); Acta Chim, Acad. Sci. Hung., 10, 227–32 (1956)); (2) a method wherein reduction and a Sandmeyer method are combined; and (3) a method wherein chlorodenitration of 2,4-dinitrofluorobenzene is involved (Khim. Kauka i Prom., 3, 404–5 (1958); Zh. Obshch. Khim., 31, 1222–6 (1961)).

Further, (4) a method of fluorinating 1,2,4-trichlorobenzene with potassium fluoride (J. Fluorine Chem., 2(1), 19–26 (1972)) or (5) a method of fluorinating p-dichlorobenzene with silver fluoride (J. Org. Chem., 45(18), 3597–603 (1980) may be mentioned.

The method (1) has a drawback that the volume efficiency of the reactor is low in addition to a disadvantage that dangerous hydrogen fluoride is used in a large amount. The method (2) is an expensive process in that not only it requires a two step reaction as shown below, but a large amount of hydrochloric acid wastes solution is produced in the second step of the Sandmeyer method and its treatment is costly. Besides, the volume efficiency is low.

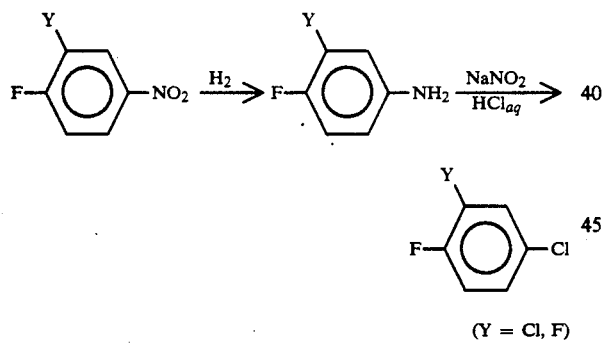

(Y = Cl, F)

The method (3) has a drawback that unreacted chlorofluoronitrobenzene is likely to be formed as a by product, and the yield is low. In the methods (4) and (5), the yield is even lower, and they are not useful as industrial processes.

The present inventors have conducted extensive researches with an aim to develop a process for industrially advantageously producing chlorofluorobenzenes from fluorine-containing nitrobenzenes and have finally completed an excellent process capable of realizing a high productivity by reducing the number of process steps.

The present invention provides a process for producing chlorofluorobenzenes, which comprises reacting fluorine-containing nitrobenzenes of the following formula (1) with chlorine gas to obtain chlorofluorobenzenes of the following formula (2):

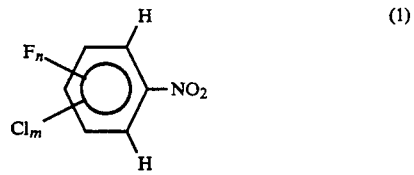

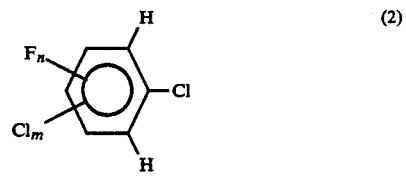

wherein n and m are integers satisfying $1 \leq n \leq 3$, $0 \leq m \leq 2$ and $1 \leq n+m \leq 3$.

Now, the present invention will be described in detail with reference to the preferred embodiments.

The fluorine-containing nitrobenzene of the formula (1) is the one having at least one fluorine attached to the benzene ring. The chlorofluorobenzene of the formula (2) is the one having at least one fluorine and at least one chlorine attached to the benzene ring, as the nitro group of the above-mentioned fluorine-containing nitrobenzene has been substituted by chlorine.

The reaction temperature in the process of the present invention varies depending upon the starting material and the reaction pressure. Typically, however, a gas phase reaction conducted at a temperature within a range of from about 300° to 600° C. is preferred. When the starting material is 3,4-difluoronitrobenzene or the like, the temperature is preferably within a range of from 380° to 450° C. The reaction may be conducted under atmospheric pressure, but may be conducted under reduced or elevated pressure.

The amount of the chlorine gas may vary depending upon the desired reaction rate, but an excess amount of the chlorine gas may be used. For example, the chlorine gas may suitably be used in an amount of from 0.1 to 20 mols, preferably from 1 to 5 mols, per mol of the starting material fluorine-containing nitrobenzene. In the case of a gas phase reaction, the residence time required for the reaction is from 0.1 to 100 seconds, preferably from 5 to 20 seconds, and the starting material is vaporized prior to being supplied to the reactor. To facilitate the vaporization, it may be diluted with a gas inert to the reaction such as nitrogen, argon or helium. Otherwise, the starting material may preliminarily dissolved in a solvent inert to the reaction, and the solution may be supplied to a vaporizer.

The reactor may be of any type, but usually a cylindrical reactor is employed.

As a process for producing chlorofluorobenzenes of the present invention, particularly advantageous is a process wherein fluorine-containing nitrobenzenes of the following formula (3) are reacted with chlorine gas to obtain chlorofluorobenzenes of the following formula (4):

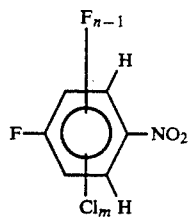

(3)

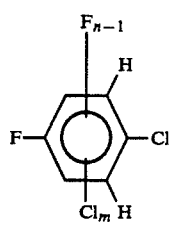

(4)

wherein n and m are integers satisfying $1 \leq n \leq 3$, $0 \leq m \leq 2$ and $1 \leq n+m \leq 3$.

Heretofore, chlorination of a nitro group of a nitrobenzene is considered to take place when a substituent having a strong electron withdrawing force such as $NO_2$, $CN$ or $CF_3$ is present at the p-position to the nitro group (U.S. Pat. No. 4,470,930), and to hardly take place when the substituent at the p-position is a substituent having a weak electron withdrawing force such as chlorine. For example, in the following reaction, it has been believed that dichlorobenzene does not form (Berichte der deutschen chemischen Geselshaft 24, 3749 (1891)).

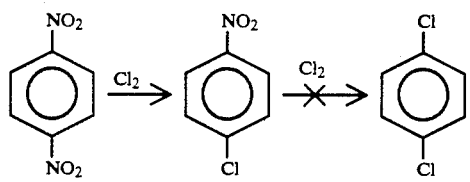

However, it has been found for the first time by the present invention that even when fluorine having a substituent constant $\sigma_p$ (an index for an electron withdrawing force; the larger the value, the larger the electron withdrawing force) smaller than that of chlorine is present at the p-position to the nitro group, chlorination of this nitro group readily takes place. Thus, it has now been made possible to conduct the reaction for introducing chlorine to the p-position to the fluorine on the benzene ring extremely advantageously.

According to the present invention, the chlorofluorobenzene may also be produced by reacting an aromatic nitro compound of the following formula (5) with a fluorinating agent to obtain a fluorine-containing nitrobenzenes of the following formula (6), which are then chlorinated.

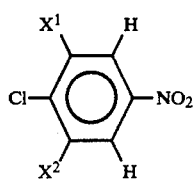

(5)

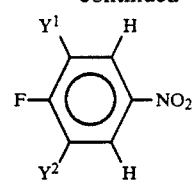

(6)

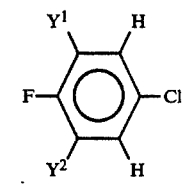

(7)

wherein each of $X^1$ and $X^2$ is H, Cl or F, and each of $Y^1$ and $Y^2$ is H, Cl or F, provided that when each of X and $X^2$ is H or F, $X^1=Y^1$ and $X^2=Y^2$, and when each of $X^1$ and $X^2$ is Cl, each of $Y^1$ and $Y^2$ is Cl or F. In the case of fluorination by means of only a fluorinating agent, such as KF, Cl for $X^1$ or $X^2$ will not usually be substituted by fluorinating agent. However, by using a fluorinating catalyst, Cl can be substituted by F.

The reaction temperature for the fluorination varies depending upon the starting material. Typically, however, the reaction temperature is suitably within a range of from about 100° to 300° C., preferably from 150° to 250° C.

As the fluorinating agent, an alkali metal fluoride is preferred. Particularly preferred is KF, RbF or CsF. It is used usually in an amount of from 1 to 3 times, preferably from 1 to 2 times, the theoretical amount required for chlorine in the aromatic nitro compounds to be substituted by fluorine.

In this reaction, a reaction solvent is not necessarily required. However, an aprotic polar solvent may be employed. Such an aprotic polar solvent may be, for example, acetonitrile, dimethylformamide, dimethylsulfoxide, sulfolane, N-methyl-2-pyrrolidone, N-cyclohexyl-2-pyrrolidone, hexamethylphosphoro triamide or 1,3-dimethyl-2-imidazolidinone. Particularly preferred is sulfolane or 1,3-dimethyl-2-imidazolidinone. There is no particular restriction as to the amount of the solvent. However, the solvent is suitably used usually in an amount of from 0.2 to 10 times, preferably from 1 to 5 times, by weight relative to the starting material aromatic nitro compound.

Further, if necessary, a phase transfer catalyst may be added. Such a phase transfer catalyst may be, for example, quaternary ammonium salts such as tetrabutyl ammonium bromide or tetramethylammonium chloride, a quaternary phosphonium salts such as tetrabutyl phosphonium bromide, or a pyridinium salt such as N-(2-ethyl-hexylamino)-4-(N',N'-dimethyl)-pyridinium.

For the reaction of the fluorine containing nitrobenzenes of the formula (6) to produce chlorofluorobenzenes of the formula (7), the above-mentioned chlorination reaction in the present invention can be employed.

Now, the present invention will be described in detail with reference to Examples. However, it should be understood that the present invention is by no means restricted by such specific Examples.

EXAMPLE 1

3,4-difluoronitrobenzene was continuously supplied to a vaporizer made of glass, vaporized and then supplied to a reactor together with a small amount of nitrogen. The molar ratio of 3,4-difluoronitrobenzene to nitrogen was 130:1. The above-mentioned gas and chlorine gas were continuously passed through the reactor made of nickel having an inner diameter of 27 mm and a length of 1,000 mm and maintained at 400° C. by a salt bath furnace. The residence time was 10 seconds, and the molar ratio of the chlorine to 3,4-difluoronitrobenzene was 1.2. The liquid cooled and condensed at the outlet, was analyzed by gas chromatography, whereby the conversion of 3,4-difluoronitrobenzene was 100%, and the selectivity for 3,4-difluorochlorobenzene was 82%.

COMPARATIVE EXAMPLE 1

(Process wherein reduction and a diazochlorination method are used in combination)

10 g of 3,4-difluoronitrobenzene was dissolved in 20 and 2 g of methanol and 10 g of concentrated hydrochloric acid and 2 g of iron powder were added thereto. The mixture was stirred at 60° C. for two hours, and then distilled to obtain 3,4-difluoroaniline. The reduction yield was 86%. To this product, 70 g of 36% hydrochloric acid was added to convert it into its salt. Under stirring, 18 g of a 25% NaNO$_2$ aqueous solution was added at 0° C. to obtain a diazonium salt. The diazonium salt was dropwise added to a hydrochloric acid solution of cupric chloride heated to 120° C., for thermal decomposition. The diazotization yield was 84%. 3,4-Difluorochlorobenzene was obtained in an overall yield of 72%.

EXAMPLE 2

The reaction was conducted in the same manner as in Example 1 except that 3-chloro-4-fluoronitrobenzene was used as the starting material, whereby the conversion of 3-chloro-4-fluoronitrobenzene was 95%, and the selectivity for 1,3-dichloro-4-fluorobenzene was 90%.

EXAMPLE 3

Into a 200 ml glass reactor equipped with a reflux condenser, 50 g of 3,4-dichloronitrobenzene, 20 g of spray-dried KF and 100 g of sulfolane were charged and reacted at 225° C. for 4.5 hours under vigorous stirring. The reaction solution was analyzed by gas chromatography, whereby the conversion of the starting material was 100%, and the selectivity for 3-chloro-4-fluoronitrobenzene was 93%.

3-Chloro-4-fluoronitrobenzene obtained by distilling this reaction solution for purification, was continuously supplied to a vaporizer made of glass, vaporized and then supplied to a reactor together with a certain amount of nitrogen. The molar ratio of 3-chloro-4-fluoronitrobenzene to nitrogen was 130:1. The above gas and chlorine gas were continuously passed through a reactor made of a nickel, having an inner diameter of 27 mm and a length of 1,000 mm and maintained at 400° C. by a salt gas furnace. The residence time was 10 seconds, and the molar ratio of chlorine to 3-chloro-4-fluoronitrobenzene was 1.2. The liquid cooled and condensed at the outlet, was analyzed by gas chromatography, whereby the conversion of 3-chloro-4-fluoronitrobenzene was 95%, and the selectivity for 1,3-dichloro-4-fluorobenzene was 90%.

EXAMPLE 4

Into a 200 ml glass reactor equipped with a reflux condenser, 50 g of 3,4-dichloronitrobenzene, 30 g of spray-dried KF, 2.5 g of N-(2-ethyl hexylamino)-4-(N',N'-dimethyl)-pyridinium chloride and 100 g of sulfolane were charged and reacted at 190° C. for 15 hours under vigorous stirring. The reaction solution was analyzed by gas chromatography, whereby the conversion of the starting material was 100%, and the selectivity for 3,4-difluoronitrobenzene was 51%.

The reaction was conducted in the same manner as in Example 3 except that 3,4-difluoronitrobenzene obtained by distilling this solution for purification, was used as the starting material, whereby the conversion of 3,4-difluoronitrobenzene was 100%, and the selectivity for 3,4-difluorochlorobenzene was 82%.

EXAMPLE 5

Into a 200 ml glass reactor equipped with a reflux condenser, 50 g of 3,4,5-trichloronitrobenzene, 20 g of spray dried KF and 100 g of sulfolane were charged and reacted at 220° C. for 4.5 hours under vigorous stirring. The reaction solution was analyzed by gas chromatography, whereby the conversion of the starting material was 95%, and the selectivity for 3,5-dichloro 4-fluoronitrobenzene was 83%.

The reaction was conducted in the same manner as in Example 3 except that 3,5-dichloro-4-fluoronitrobenzene obtained by distilling this reaction solution for purification, was used as the starting material, whereby the conversion of 3,5-dichloro-4-fluoronitrobenzene was 94%, and the selectivity for 1,3,5-trichloro-2-fluorobenzene was 92%.

EXAMPLE 6

Into a 200 ml glass reactor equipped with a reflux condenser, 50 g of 3,4,5-trichlorobenzene, 40 g of spray dried KF, 5 g of tetra(n-butyl)phosphonium bromide and 100 g of sulfolane were charged and reacted at 200° C. for 15 hours under vigorous stirring. The reaction solution was analyzed by gas chromatography, whereby the conversion of the starting material was 81%, and the selectivity for 3-chloro-4,5-difluoronitrobenzene was 65%.

The reaction was conducted in the same manner as in Example 3 except that 3-chloro-4,5-difluoronitrobenzene obtained by distilling this reaction solution for purification, was used as the starting material, whereby the conversion of 3-chloro-4,5-difluoronitrobenzene was 96%, and the selectivity for 1,3-dichloro-4,5-difluorobenzene was 60%.

According to the present invention, 1,3-dichloro-4-fluorobenzene or 3,4-difluorochlorobenzene, useful as intermediates for pharmaceuticals and agricultural chemicals, particularly as intermediates for synthetic antimicrobial agents can be obtained advantageously on an industrial scale.

We claim:

1. A continuous process for producing chlorofluorobenzenes, which comprises reacting the nitrobenzene of formula (6) in the vapor phase with chlorine gas at 300°–600° C. to obtain a chlorofluorobenzene of formula (7):

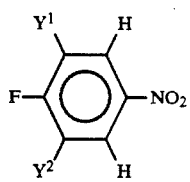 (6)

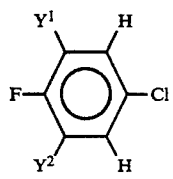 (7)

wherein each of Y¹ and Y² is H or F.

2. A process for producing chlorofluorobenzenes, which comprises reacting aromatic nitro compounds of formula (5) with a fluorinating agent to obtain fluorine-containing nitrobenzenes having formula (6), and then reacting the nitrobenzene of formula (6) in the vapor phase with chlorine gas at 300°–600° C. to obtain a chlorofluorobenzene of formula (7):

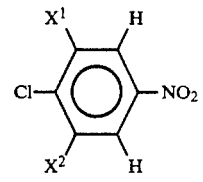 (5)

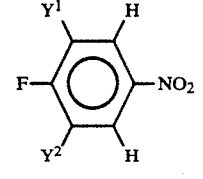 (6)

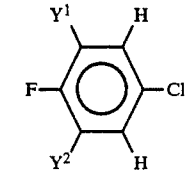 (7)

wherein each of X¹, X², Y¹ and Y² is H or F.

* * * * *